United States Patent [19]

Andrews

[11] Patent Number: 4,614,035

[45] Date of Patent: Sep. 30, 1986

[54] HAND HELD APPARATUS FOR DESTROYING HYPODERMIC NEEDLES

[76] Inventor: William M. Andrews, 12411 Renwick, Houston, Tex. 77035

[21] Appl. No.: 627,201

[22] Filed: Jul. 2, 1984

[51] Int. Cl.⁴ .......................... B23D 17/08; B26D 5/10
[52] U.S. Cl. ........................................ 30/124; 30/131; 83/167
[58] Field of Search ................. 30/124, 131, 113, 134; 83/167, 580, 926 B

[56] References Cited

U.S. PATENT DOCUMENTS

| | | | |
|---|---|---|---|
| 3,067,514 | 12/1962 | Main | 30/124 |
| 3,404,593 | 10/1968 | Arcarese | 83/167 |
| 3,736,824 | 6/1973 | Dunnican | 83/167 |
| 4,255,996 | 3/1981 | Choksi | 83/167 |
| 4,275,628 | 6/1981 | Greenhouse | 83/167 |
| 4,404,881 | 9/1983 | Hanifl | 83/167 |

*Primary Examiner*—Jimmy C. Peters
*Attorney, Agent, or Firm*—Robert J. Marett

[57] ABSTRACT

A hand carried, hand operated portable apparatus for destroying hypodermic needles is disclosed herein comprising a housing having a lever arm pivotably mounted on the housing engaging a shearing blade which travels through an internal channel through the top of the housing. A removable container having a longitudinal groove formed by inwardly disposed wall members is press fitted into the housing. A needle from a hypodermic syringe is placed in the longitudinal groove and pressed into the interior of the container in such a manner that the needle remains inside the container after it is cut from the hypodermic syringe.

20 Claims, 28 Drawing Figures

U.S. Patent  Sep. 30, 1986  Sheet 1 of 4  4,614,035
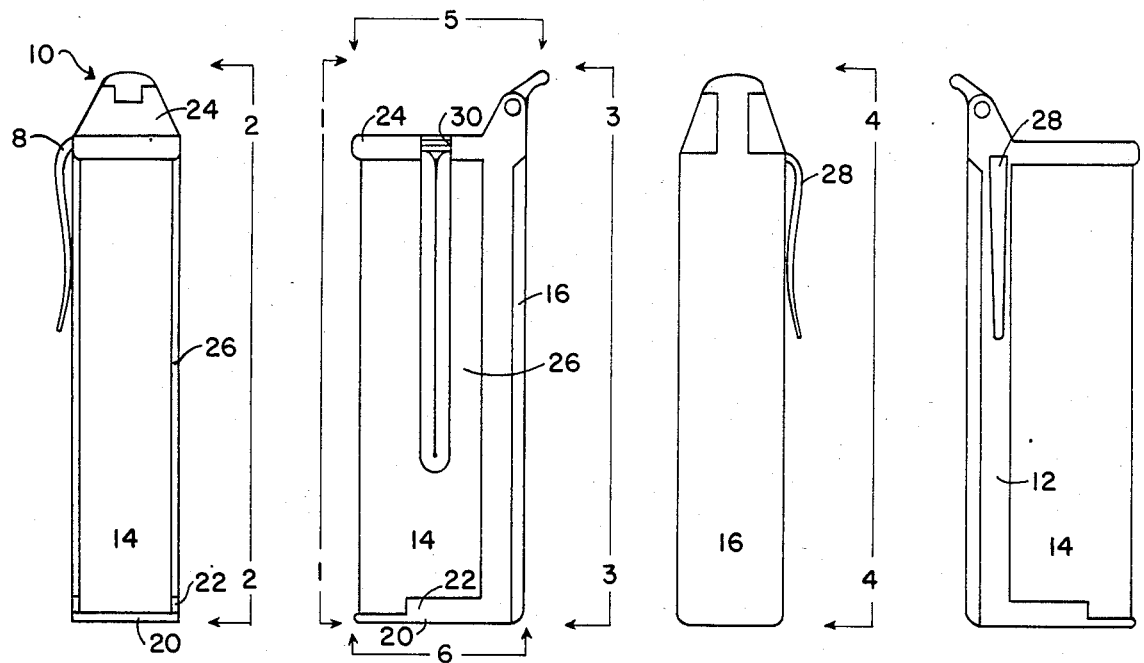
Fig. 1   Fig. 2   Fig. 3   Fig. 4
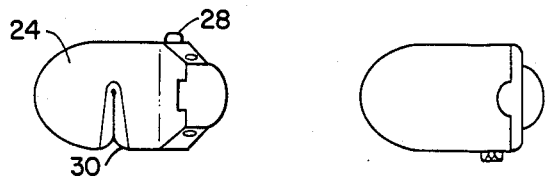
Fig. 5   Fig. 6
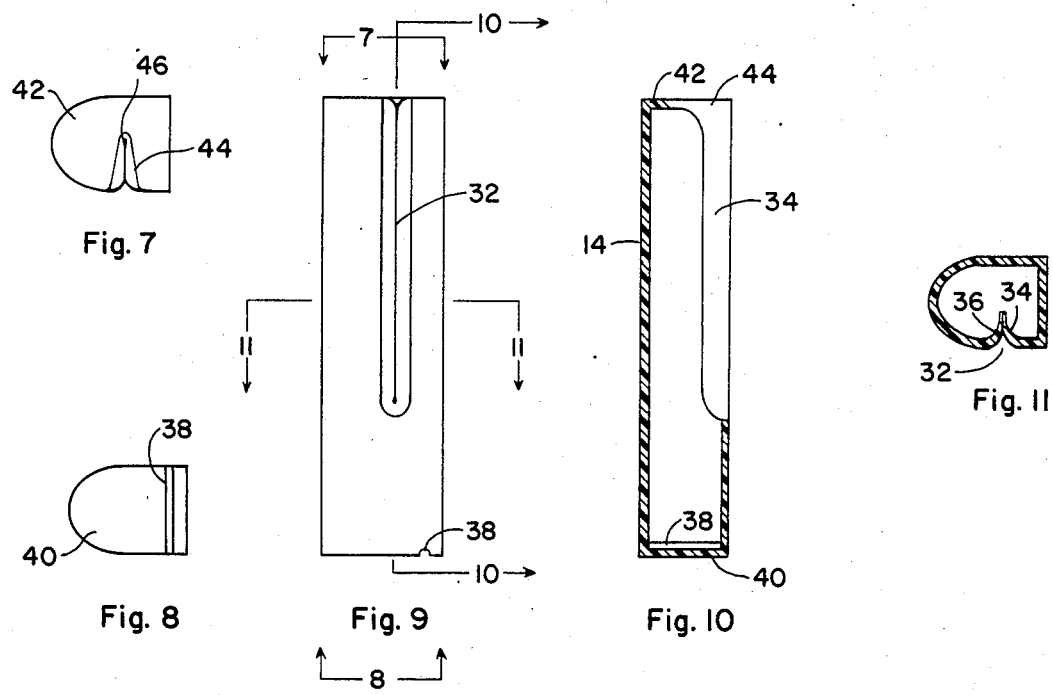
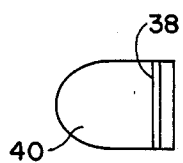
Fig. 7
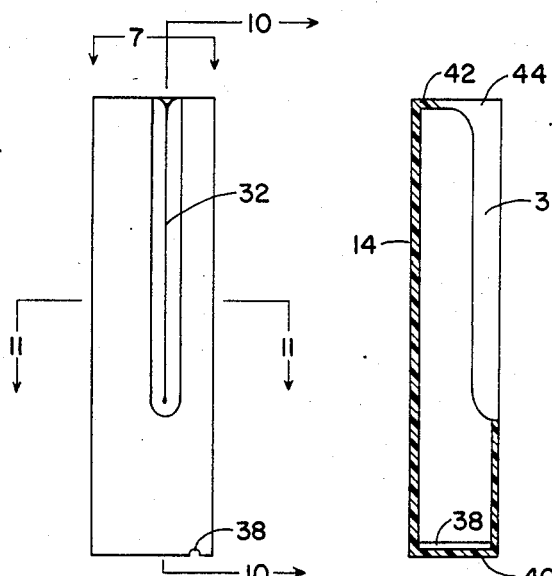
Fig. 8   Fig. 9   Fig. 10
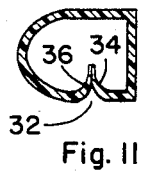
Fig. 11

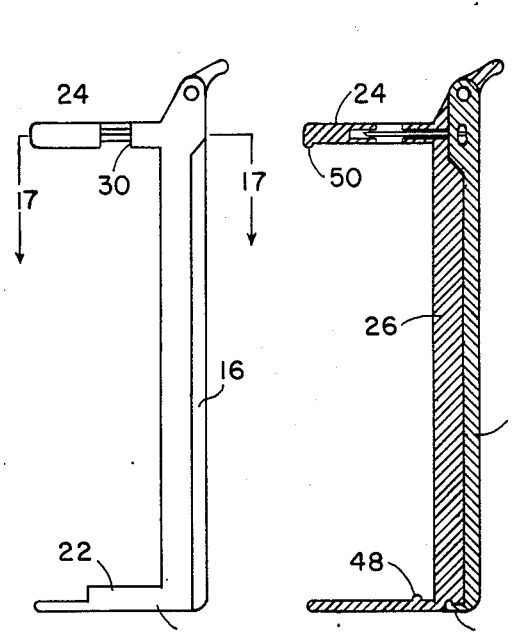
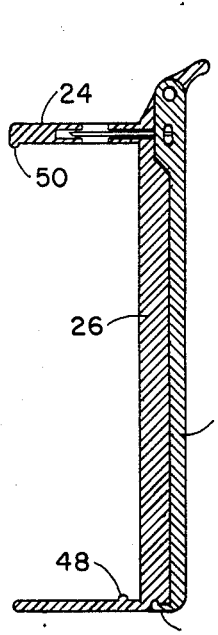
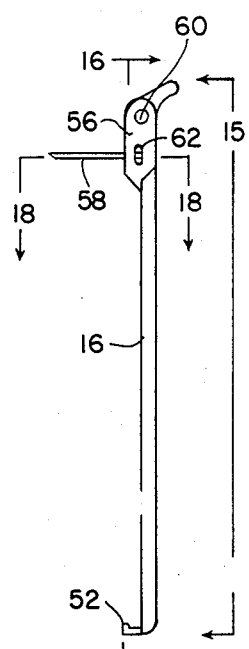
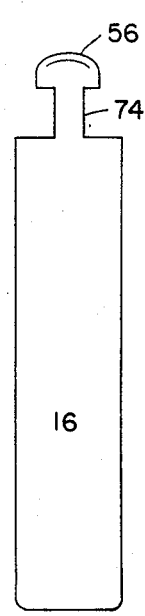
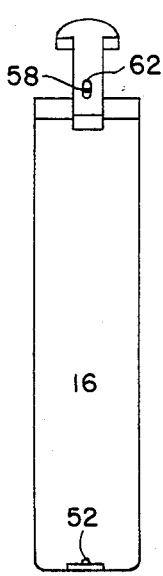
Fig. 12    Fig. 13    Fig. 14    Fig. 15    Fig. 16
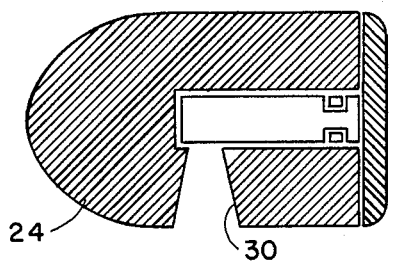
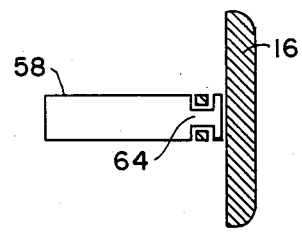
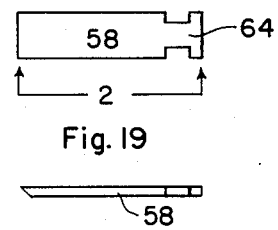
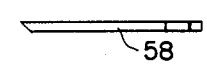
Fig. 17    Fig. 18    Fig. 19    Fig. 20
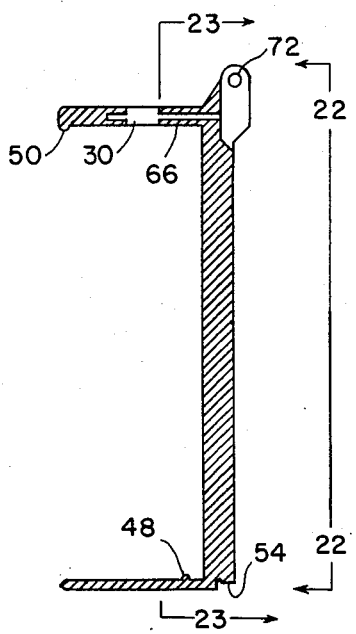
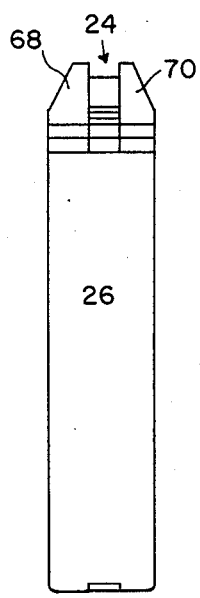
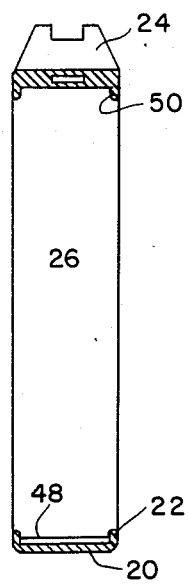
Fig. 21    Fig. 22    Fig. 23

HAND HELD APPARATUS FOR DESTROYING HYPODERMIC NEEDLES

BACKGROUND OF THE INVENTION

1. Field of the Invention

The present invention generally relates to devices for destroying hypodermic needles and, more particularly to a hand carried, hand operated portable apparatus for destroying hypodermic needles and safely storing the spent needles in a disposable removal container.

2. Description of the Prior Art

For various health and legal reasons, such as the prevention of the spread of disease, cross contamination of patients and the prevention of illegal drug traffic, it is important that a hypodermic needle be destroyed after each use. In fact several states have laws that require doctors, nurses and other health care providers to destroy hypodermic needles immediately after use. This not only creates a substantial disposal problem but also creates a serious handling problem. Incidents are happening everyday in health care facilities where persons are being scratched by used needles and becoming ill and not knowing what the illness is related to. Accidental needle scratch injuries to health care personnel have become so extensive due to the careless handling of used needles that a major health care problem now exists among major hospitals. Committees have been formed within hospitals to specifically address the issue of lowering the number of needle scratch incidents among personnel in their facilities.

Apparatuses are in the prior art for destroying hypodermic needles. Representative of the prior art devices are those described in U.S. Pat. Nos. 4,315,448; 4,275,628; 3,469,750; 4,255,966; and 3,683,733. Although these devices will destroy a hypodermic needle, they are fairly substantial in size and therefore are required to be placed in a central location for use such as at each nurses' station within a hospital. These devices have serious drawbacks in that after each injection the nurse must bring back the used hypodermic needle to the nurses' station to these devices for destruction. Needle scratch incidents usually occur after the injection is given to the patient and before the nurse has an opportunity to return to the nurses' station to destroy the needle. It would therefore be desirable to have a portable apparatus that health care providers could carry with them to allow them to destroy the hypodermic needle immediately after the injection.

Recognizing the need to have health care personnel carry portable devices to detroy needles after their use, hand operated portable devices were developed. One hand carried, hand operated portable device for destroying hypodermic needles is described and illustrated in U.S. Pat. No. 3,914,865 to Andrew A. Oakes. The Oakes patent discloses a hand carried, hand operated portable device for destroying hypodermic needles. The device comprises a portable housing enclosing a needle chamber for storing the used needles after they were cut from the hypodermic syringe. Once the comparment is filled with used needles the entire apparatus is discarded.

While this apparatus, or variations of it, will certainly destroy a hypodermic needle, it does have some drawbacks. One major drawback is that the hypodermic needle must be inserted through a small orifice in an entry portal. This requires steady hands to prevent the needle from jumping out of the entry portal and scratching a finger of the hand holding the portable device. Health care personnel are usually very busy and very often are in high stress situations where injections must be given quickly and the hypodermic needle disposed of quickly. When one is very busy or in a high stress situation, it is very difficult sometimes to try to insert a small diameter needle through a small diameter orifice. This is tantamount to trying to thread a needle. Very often what happens is that the health care provider is in a hurry and tries to force the needle through the orifice without taking the necessary time to accurately line the needle up with the orifice which causes the needle to jump out of the entry portal and scratch a finger of the hand holding the device. Another drawback of this apparatus is that once the internal compartment is full of used needles, the entire apparatus must be discarded. However, the biggest problem associated with hand held, hand operated portable devices for destroying hypodermic needles is insertion of the needle into the device without scratching one's finger of the hand holding the device.

Consequently, a need exists for improvements in hand carried, hand operated portable devices for destroying hypodermic needles which would result in faster and safer insertion of the needle into the device for destruction thereof and therefore reducing needle scratch incidents among persons who give hypodermic injections.

SUMMARY OF THE INVENTION

The invention described herein comprises a hand carried, hand operated portable apparatus for destroying hypodermic needles comprising a housing adapted to receive a disposable container which snaps into the housing. Along one side of the disposable container is a longitudinal groove running along the surface formed by inwardly disposed adjacent wall members defining an opening. The disposable container is snap fitted into the housing and aligns with another opening on the top of the housing. The hypodermic needle is placed along side the disposable container in such a manner that the entire needle rests in the longitudinal groove of the container thus keeping the tip of the used needle away from any fingers of the hand holding the device. The needle is then forced sideways into the container and through the opening at the top of the housing. A lever and cutting means, which are a part of the housing, are then used to cut the needle off os the hypodermic syringe. The cut needle then falls into the interior of the disposable container for safe keeping. After the container becomes full, it is snapped apart from the housing and disposed of and a new empty disposable container is snap fitted into the housing for use again.

An important feature of the invention is that the needle of the hypodermic syringe is inserted into the container sideways through a longitudinal groove thus making it easier to insert the needle into the container and cutting means without the risk associated with trying to insert a needle through a very small orifice opening.

BRIEF DESCRIPTION OF THE DRAWINGS

FIG. 1 is a front elevation view of the apparatus according to the present invention.

FIG. 2 is a side elevation view taken along lines 2—2 of FIG. 1.

FIG. 3 is a rear elevation view taken along lines 3—3 of FIG. 2.

FIG. 4 is the other side elevation view taken along lines 4—4 of FIG. 3.

FIG. 5 is a plan view taken along lines 5—5 of FIG. 2.

FIG. 6 is a bottom view taken along lines 6—6 of FIG. 2.

FIG. 7 is a plan view of the removable container taken along lines 7—7 of FIG. 9.

FIG. 8 is a bottom view of the removable container taken along lines 8—8 of FIG. 9.

FIG. 9 is a side elevation view of the removable container showing the longitudinal groove.

FIG. 10 is a cross sectional detailed view of the removable container taken along lines 10—10 of FIG. 9 showing an inwardly disposed wall member forming one-half of the longitudinal groove.

FIG. 11 is a cross sectional detailed view of the removable container taken along lines 11—11 of FIG. 9 showing adjacent inwardly disposed wall members forming the longitudinal groove.

FIG. 12 is a side elevation view of the housing and lever assembly with the removable container removed.

FIG. 13 is a cross sectional view of the housing and lever assembly of FIG. 12.

FIG. 14 is a side elevation view of the lever assembly shown in isolation of FIG. 12.

FIG. 15 is a rear elevation view of the lever assembly taken along lines 15—15 of FIG. 14.

FIG. 16 is a front elevation view of the lever assembly taken along lines 16—16 of FIG. 14.

FIG. 17 is a cross sectional view of the top member of the housing taken along lines 17—17 of FIG. 12.

FIG. 18 is a cross sectional detailed view of the shearing blade taken along lines 18—18 of FIG. 14.

FIG. 19 is a plan view of the shearing blade.

FIG. 20 is a side elevation view of the shearing blade taken along lines 20—20 of FIG. 19.

FIG. 21 is another cross sectional side elevation view of the housing without the lever assembly and the removable container attached thereto.

FIG. 22 is a rear elevation view of the housing taken along lines 22—22 of FIG. 21.

FIG. 23 is a front elevation view of the housing taken along lines 23—23 of FIG. 21.

DESCRIPTION OF THE PREFERRED EMBODIMENT

Figure 24:
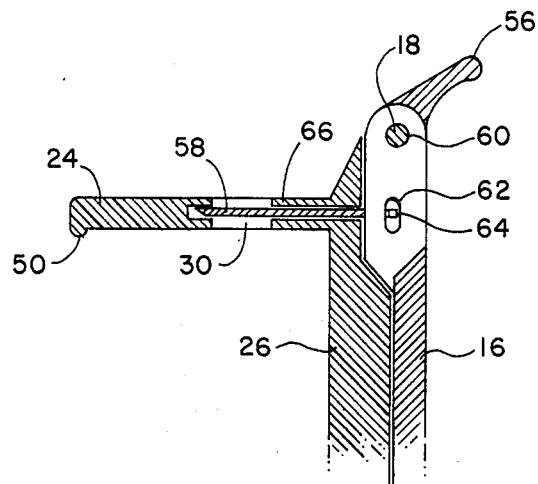
FIG. 24 is a cross sectional detailed view of the top member of the housing and the lever assembly showing the shearing blade extending through the internal channel of the top member of the housing.

Referring initially to FIG. 29, there is illustrated a hand held apparatus 10 of the invention which comprises a housing 12 adapted to receive a removable container 14 and further comprising a lever arm 16 pivotally mounted on said housing 12 by means of pin 18.

FIGS. 1-6 illustrate show additional details of the apparatus 10 according to the present invention. It is seen that the housing 12 further comprises a bottom member 20 having upwardly extending sides 22, a top member 24 spaced apart from the bottom member 20 by means of a wall section 26 and a clip 28 attached to the housing 12 so that one can conveniently clip the apparatus 10 inside a pocket when the apparatus is not being used. Top member 24 has an opening 30 which will be described in more detail below.

FIGS. 7-11 illustrate the various details of the removable container 14. Removable container 14 is sized to pressure fit within the housing 12 between the top member 24, between the upwardly extending side of 22 of the bottom member 20 and against the wall section 26. A longitudinal groove 32 is disposed along one side of the removable container 14 and is formed by the ends of adjacent inwardly disposed wall members 34 and 36 curving inward. A slot 38 is disposed on the bottom wall member 40, the function of which will be described later in this specification. The removable container 14 has a top member 42 having an opening 44 defined by the continuation of the inwardly disposed wall member 34 and 36 defining a small orifice 46.

FIGS. 12-16 illustrate further details of the housing 12 and the lever arm 16. A raised rib 48 is disposed on the top of the bottom member 20 and runs between the upwardly extending sides 22. Top member 24 has an extending lip 50 around the periphery of the under side of the top member 24. The raised rib 48 and the extending lip 50 help hold the removable container 14 within the housing 12 when the removable container 14 is pressed between the bottom member 20 and the top member 24 of the housing 12. The lever arm 16 has an extending rib 52 which snaps into a notch 54 on the bottom end of the wall section 26 when the lever arm 16 is not in use. Lever arm 16 has a top section 56 which incorporate a shearing blade 58. Top section 56 has a first bore 60 to receive the pin 18 extending through the top member 24 of the housing 12 so that lever arm 16 will pivot around the pin 18. A second bore 62 is incorporated into the top section 56 to hold the "T" shaped end 64 of the shearing blade 58.

Figure 25:
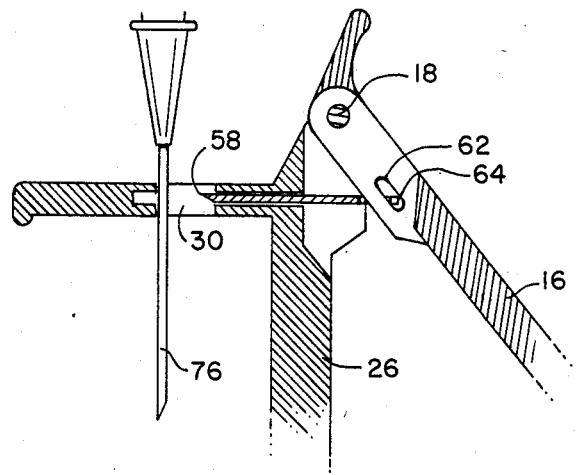
FIG. 25 is a cross sectional detailed view of the top member of the housing and the lever assembly extended prior to shearing a needle extended through the top member of the housing.
Figure 26:
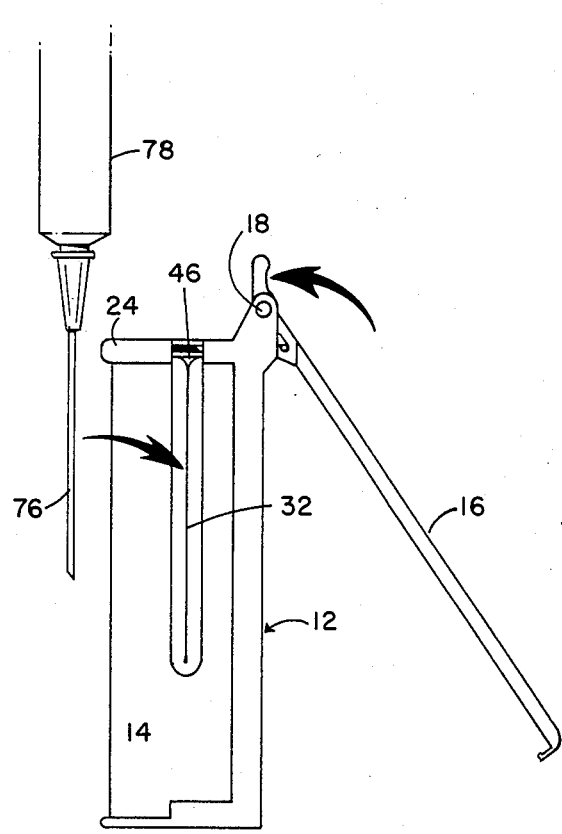
FIG. 26 is a side elevation view showing the lever assembly extended prior to the insertion of a hypodermic needle into the longitudinally groove of the removable container.
Figure 27:
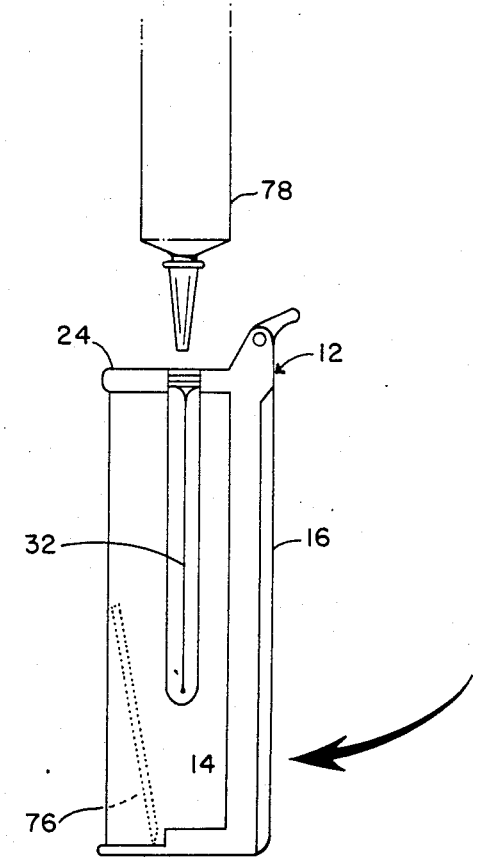
FIG. 27 is a side elevation view of the apparatus according to the present invention illustrating the lever arm in the closed position and showing in phantom view the sheared off needle within the removable container.
Figure 28:
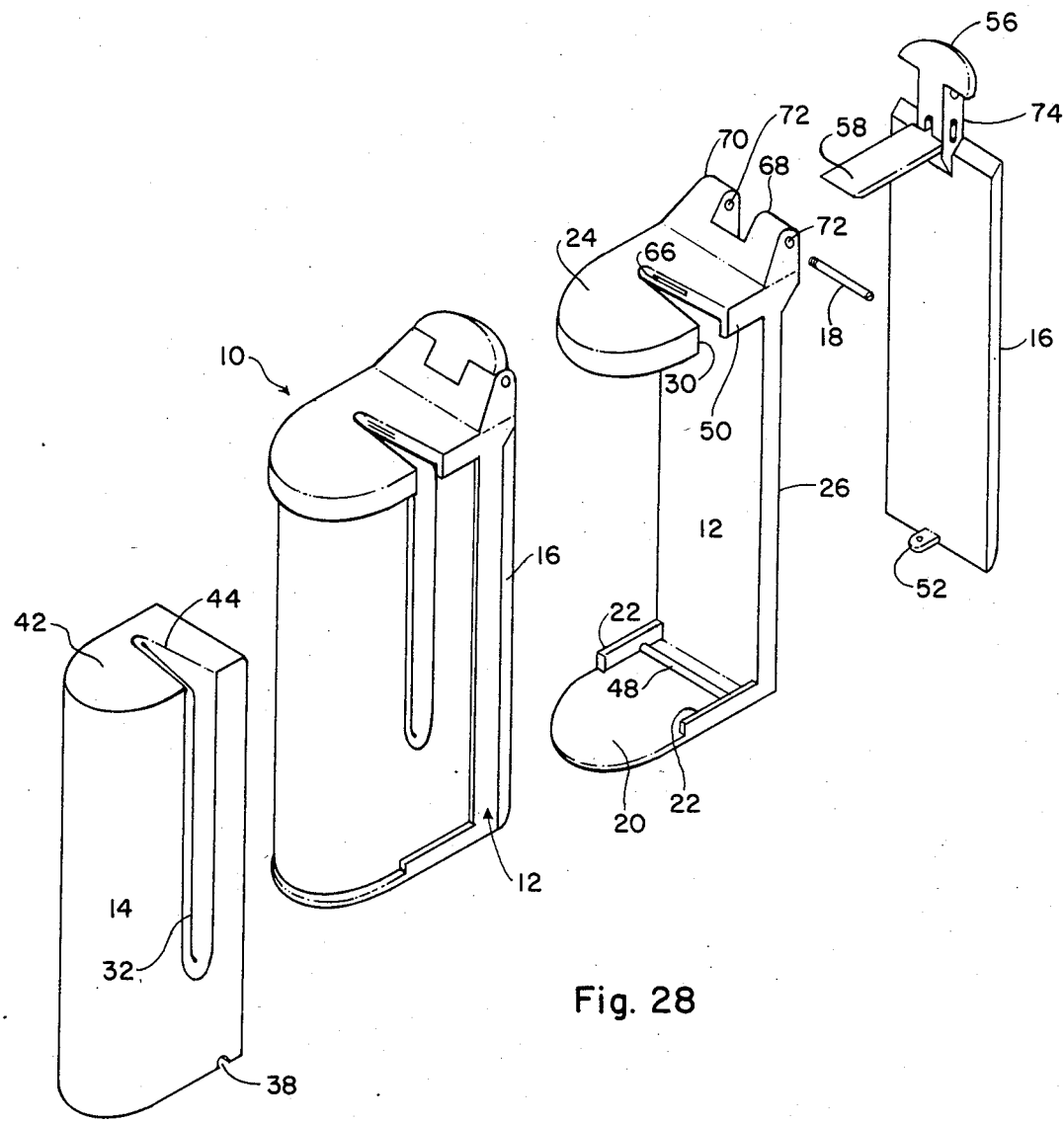
FIG. 28 is an exploded view of the apparatus according to the present invention.

FIGS. 21-23 illustrate further details of the housing 12. An internal channel 66 is incorporated into the top member 24 so that the shearing blade 58 will ride through the channel 66 into the opening 30 of the top member 24 of the housing 12. Top member 24 further has two extending members 68 and 70 having a hole 72 extending through both extending members to receive the pin 18. Lever arm 16 has a narrow neck 74, as illustrated in FIG. 15, which is placed between extending members 68 and 70 of the top member 24 and aligned in such a way so that pin 18 extends through hole 72 of the top member 24 and through first bore 60 of the top section 56 in order that lever arm 16 can pivot about pin 18 causing the shearing blade 58 to travel in and out of the internal channel 66. FIGS. 24 and 25 illustrate the pivot action of the lever arm 16 and the manner in which the shearing blade 58 moves within the internal channel 66 in order to shear a needle 76 from a hypodermic syringe 78. FIGS. 26 and 27 further illustrate the method in which a needle is sheared off. The lever arm 16 is pivoted about the pin 18 away from the housing 12 thus sliding the shearing blade 58 away from the opening 30 in the top member 24. When the removable container 14 is inserted into the housing 12, the longitudinal groove 32 aligns with the opening 30 in the top member 24.

A hypodermic syringe 78 is placed along side the apparatus 10 in such a manner that the needle 76 lies in the longitudinal groove 32 of the removable container 14. The lever arm 16 is rotated outward causing the shearing blade 58 to move away from the opening 30 through the channel 66. The needle 76 is then pushed against the adjacent inwardly disposed wall members 34 and 36 thus allowing the needle 76 to enter the interior of the removable container 14 extending through the orifice 46 and further extending through the opening 30. When the lever arm 16 is rotated down toward the housing 12, the shearing blade 58 enters the opening 30 and shears off the needle 76 causing it to drop to the bottom of the removable container 14. When the removable container 14 is full, it can be replaced with a new empty container without the necessity of discarding the entire apparatus.

While the invention has been described with reference to a preferred embodiment, it will be obvious to one skilled in art that modifications and variations of the invention may be constructed and employed without departing from the scope of the invention. The scope of the invention is defined in the following claims.

I claim:

1. An apparatus for cutting the needle off a hypodermic syringe and safely storing the spent needle comprising:
   a housing;
   a removable container mounted within said housing having a wall member with a longitudinal groove on its surface;
   a lever arm having one end pivotly mounted on said housing;
   cutting means, mounted on said lever arm and extending into said housing, for cutting the needle when the needle is placed into the housing and into the removable container and the lever arm is pivoted toward the housing.

2. An apparatus as defined in claim one wherein said removable container further includes:
   a top wall member, attached to said wall member, having an opening defined by the continuation of the longitudinal groove of said wall member;
   a bottom wall member, having a slot therein, attached to said wall member.

3. The apparatus as defined in claim two wherein said housing includes:
   a top member having an opening and an internal channel, adjacent to said opening, to receive the cutting means.

4. The apparatus as defined in claim three wherein said housing further includes:
   a downwardly extending lip positioned on said top member to hold said removable container within said housing.

5. The apparatus as defined in claim four wherein said housing includes:
   a pin positioned through said top member of said housing and through said lever arm for said lever arm to pivot around.

6. The apparatus as defined in claim five wherein the housing includes:
   a wall section having a notched end connected to said top member having a notched end adjacent to said lever arm.

7. The apparatus as defined in claim six wherein the housing further includes:
   a bottom member connected to said wall section having upwardly extending sides to further hold said removable container within said housing.

8. The apparatus as defined in claim seven wherein the housing further includes:
   a raised rib mounted on said bottom member to further hold said removable container within said housing by fitting into the slot of the bottom wall member of said removable container.

9. The apparatus as defined in claim eight wherein said lever arm includes:
   an extending rib mounted on one end to snap into the notched end of said wall section to hold said lever arm next to said wall section when said lever arm is not being used.

10. The apparatus as defined in claim nine wherein said cutting means includes:
    a shearing blade, connected to said lever arm and extending through said internal channel of said top member of said housing.

11. An apparatus for cutting the needle off of a hypodermic syringe and safely storing the cut needle comprising:
    means for holding a removable container;
    a removable container snap fitted into said holding means having a wall member with a longitudinal groove on its surface for receiving the needle of the hypodermic syringe;
    means for cutting said needle mounted on said holding means.

12. The apparatus as defined in claim one wherein said removable container further includes:
    a top wall member connected to said wall member having an opening, for the needle to extend through, formed by the continuation of said longitudinal groove;
    a bottom wall member connected to said wall member having a slot formed therein.

13. The apparatus as defined in claim twelve wherein said holding means includes:
    a top member having an opening and a channel, adjacent to said opening;
    a wall section connected to said top member;
    a bottom member, connected to said wall section, having a slot disposed therein.

14. The apparatus as defined in claim thirteen wherein said holding means further includes:
    an extending lip, mounted on said top member, extending toward the bottom member.

15. The apparatus as defined in claim fourteen wherein said holding means further includes:
    a plurality of extending sides mounted on said bottom member extending toward the top member;
    a raised rib, mounted on the bottom member, for snapping into the slot of the bottom wall member of said removable container.

16. The apparatus as defined in claim fifteen wherein said cutting means includes:
    a lever arm pivolty mounted on one end to said top member of said holding means.

17. The apparatus as defined in claim sixteen wherein said cutting means further includes:

a shearing blade mounted on said lever arm extending through said channel and into said opening of said top member.

18. The apparatus as defined in claim seventeen wherein said cutting means further includes:
an extending rib, mounted on the other of said lever arm, to snap fit under the wall section of said holding means when the lever arm is not in use.

19. An apparatus for cutting the needle off a hypodermic syringe and safely storing the spent needle comprising:
a top member having an opening and a channel adjacent to said opening;
a wall section, connected to said top member, having a notch on one end;
a bottom member, connected to said wall section, having sides extending toward the top member;
a raised rib mounted on said bottom member;
an extending lip, mounted on said top member, positioned toward said bottom member;
a lever arm, pivotly mounted on one end to said top member, having a bore on the end pivotly mounted and an extending rib on the other end to snap fit into the notch on the end of the wall section;
a shearing blade, snap fitted into the bore on said lever arm, extending into the channel of said top member;
a removable container snap fitted between said top member and said bottom member for storing the needle after it is cut having a wall member with a longitudinal groove on its surface for the needle to be placed in and slid through sideways into the interior of the wall member.

20. The apparatus as defined in claim one wherein said removable container further includes:
a top wall member connected to said wall member having an opening, for the needle to extend through, formed by the continuation of said longitudinal groove;
a bottom wall member, connected to said wall member, having a slot formed therein to fit into the raised rib on said bottom member.

* * * * *